(12) United States Patent
Wang et al.

(10) Patent No.: US 7,697,741 B2
(45) Date of Patent: Apr. 13, 2010

(54) COMPRESSION AND DECOMPRESSION OF MEDICAL IMAGES

(75) Inventors: Gang Wang, Frederick, MD (US); Bruce Jackson, Mukilteo, WA (US)

(73) Assignee: Microsoft Corporation, Redmond, WA (US)

(*) Notice: Subject to any disclaimer, the term of this patent is extended or adjusted under 35 U.S.C. 154(b) by 802 days.

(21) Appl. No.: 11/565,899

(22) Filed: Dec. 1, 2006

(65) Prior Publication Data

US 2008/0130967 A1    Jun. 5, 2008

(51) Int. Cl.
*G06K 9/00* (2006.01)
*A61B 6/00* (2006.01)

(52) U.S. Cl. ............ 382/128; 382/235; 378/21

(58) Field of Classification Search ........ 382/100, 382/128, 129, 130, 131, 132, 133, 134, 155, 382/168, 180, 181, 209, 219, 224, 232, 233, 382/234, 240, 235, 248, 243, 254, 274, 276, 382/286, 291, 294, 305, 312; 378/4, 21, 378/23; 347/5; 709/206
See application file for complete search history.

(56) References Cited

U.S. PATENT DOCUMENTS

| | | | |
|---|---|---|---|
| 4,768,099 A | | 8/1988 | Mukai et al. |
| 5,724,582 A | | 3/1998 | Pelanek et al. |
| 6,134,350 A | * | 10/2000 | Beck ................ 382/240 |
| 6,912,317 B1 | | 6/2005 | Barnes et al. |
| 6,937,767 B1 | * | 8/2005 | Burak et al. ........... 382/232 |
| 7,068,848 B2 | * | 6/2006 | Park et al. ............. 382/240 |
| 7,286,712 B2 | * | 10/2007 | Lee et al. ............. 382/248 |
| 7,606,861 B2 | * | 10/2009 | Killcommons et al. ...... 709/206 |
| 2003/0160834 A1 | * | 8/2003 | Yamano et al. ............. 347/5 |
| 2005/0002547 A1 | | 1/2005 | Torre-Bueno |
| 2005/0207658 A1 | | 9/2005 | Schofield |
| 2006/0053004 A1 | | 3/2006 | Ceperkovic et al. |

OTHER PUBLICATIONS

Tzannes, A., Compression of 3-dimensional medical image data using part 2 of JPEG 2000, available at http://medical.nema.org/Dicom/minutes/WG-04/2004/2004-02-18/3D_compression_RSNA_2003_ver2.pdf.
Gokturk, S. B., C. Tomasi, B. Girod, C. Beaulieu, Medical image compression based on region of interest, with application to colon CT images, Proc. 23rd Annual Int. Conf. IEEE Eng'g in Med. and Biology Soc'y, Istanbul, Turkey, Oct. 2001, vol. 3, pp. 2453-2456.
Pearlman, W., Medical Image Compression Systems, Center for Next Generation Video, Rensselaer Polytechnic Institute, Dec. 11, 2001.

* cited by examiner

*Primary Examiner*—Seyed Azarian
(74) *Attorney, Agent, or Firm*—Lyon & Harr, LLP; Richard T. Lyon

(57) ABSTRACT

A medical image compression and decompression technique is presented which exploits the special characteristics of medical images so as to increase the achievable compression ratio over existing generic image compression techniques. In general, the presented technique categorizes medical images based on the type of images. Medical images within the same category will typically have a very high level of similarity to each other. For each category, a type of standard image is computed which represents the typical characteristics of images within a category. For each image being compressed, only the difference between the image and the standard image is compressed. Due to the high level of similarity between images in the same category, the aforementioned difference is typically small and therefore a high compression ratio can be achieved.

20 Claims, 8 Drawing Sheets

COMPRESSION AND DECOMPRESSION OF MEDICAL IMAGES

BACKGROUND

Current medical imaging techniques produce digital images that are invaluable for diagnosis and treatment of patients. For example, current medical imaging techniques include X-ray and angiography, computed radiography (CR), computed tomography (CT), magnetic resonance imaging (MRI), positron emission tomography (PET), ultrasound, and so on. However, these images typically contain large amounts of data, thereby causing problems in storing and archiving them. In addition, the large image files generated from medical images must be transferred from one location to another, or between devices (such as between an imaging device and a computer for further processing).

In order to mitigate the problems associated with storing and transferring medical images, they are routinely compressed. However, existing compression techniques used to compress medical images are generic in that they are designed to handle any image and are not tailored to medical images. As such these techniques fail to take into account the special characteristics of medical images that could be exploited to achieve higher compression ratios.

SUMMARY

The present medical image compression and decompression technique exploits the special characteristics of medical images so as to increase the achievable compression ratio over existing generic image compression techniques. In general, the present technique categorizes medical images based on the type of images. Medical images within the same category will typically have a very high level of similarity to each other. For each category, a type of standard image is computed which represents the typical characteristics of images within a category. For each image being compressed, only the difference between the image and the standard image is compressed. Due to the high level of similarity between images in the same category, the aforementioned difference is typically small and therefore a high compression ratio can be achieved.

More particularly, one embodiment of the present medical image compression technique involves first computing a set of base images from a larger group of source medical images belonging to a same category as a medical image being compressed. These base images in the set substantially capture the variance exhibited amongst the group of source images and are orthogonal to each other. The set of base images corresponds to the aforementioned standard image in this embodiment of the technique. Next, a difference between the medical image being compressed and the base images in the computed set is determined. The difference is compressed to produce difference data representing the compressed medical image. The compressed difference data can then be stored or transferring as desired.

With regard to decompressing a medical image compressed in the manner described above, in one embodiment of the present technique this involves first obtaining the set of base images belonging to a same category as the compressed medical image, and then decompressing the compressed difference found in the compressed difference data representing the image. This decompressed difference is combined with the set of base images to generate the decompressed medical image.

It is noted that while the foregoing limitations in existing medical image compression and decompression techniques described in the Background section can be resolved by a particular implementation of the present technique, this is in no way limited to implementations that just solve any or all of the noted disadvantages. Rather, the present medical image compression and decompression technique has a much wider application as will become evident from the descriptions to follow.

It should also be noted that this Summary is provided to introduce a selection of concepts, in a simplified form, that are further described below in the Detailed Description. This Summary is not intended to identify key features or essential features of the claimed subject matter, nor is it intended to be used as an aid in determining the scope of the claimed subject matter. In addition to the just described benefits, other advantages of the present invention will become apparent from the detailed description which follows hereinafter when taken in conjunction with the drawing figures which accompany it.

DESCRIPTION OF THE DRAWINGS

The specific features, aspects, and advantages of the present invention will become better understood with regard to the following description, appended claims, and accompanying drawings where:

DETAILED DESCRIPTION

In the following description of embodiments of the present invention reference is made to the accompanying drawings which form a part hereof, and in which are shown, by way of illustration, specific embodiments in which the invention may be practiced. It is understood that other embodiments may be utilized and structural changes may be made without departing from the scope of the present invention.

1.0 THE COMPUTING ENVIRONMENT

Before providing a description of embodiments of the present medical image compression and decompression technique, a brief, general description of a suitable computing environment in which portions thereof may be implemented will be described. The present technique is operational with numerous general purpose or special purpose computing systems environments or configurations. Examples of well known computing systems, environments, and/or configurations that may be suitable include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

Figure 1:
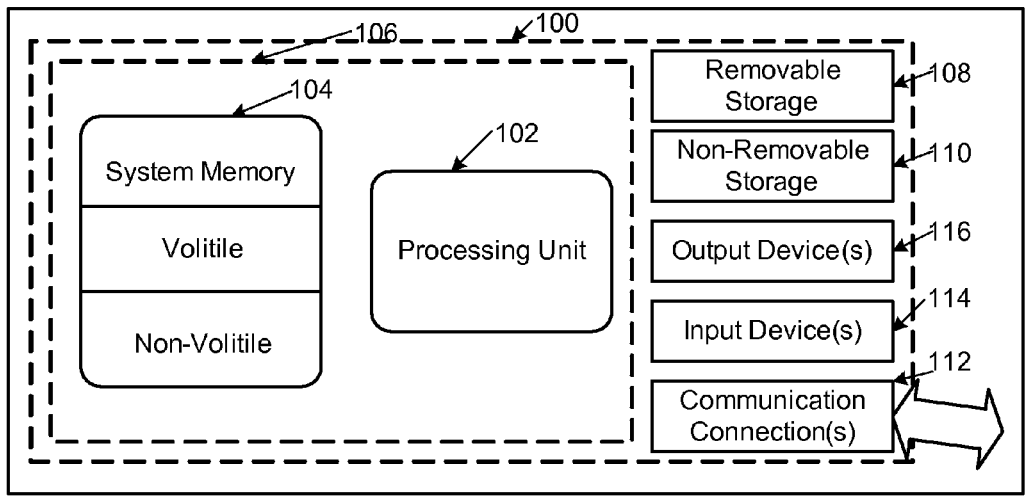
FIG. 1 is a diagram depicting a general purpose computing device constituting an exemplary system for implementing the present invention.

FIG. 1 illustrates an example of a suitable computing system environment. The computing system environment is only one example of a suitable computing environment and is not intended to suggest any limitation as to the scope of use or functionality of the present medical image compression and decompression technique. Neither should the computing environment be interpreted as having any dependency or requirement relating to any one or combination of components illustrated in the exemplary operating environment. With reference to FIG. 1, an exemplary system for implementing the present medical image compression and decompression technique includes a computing device, such as computing device 100. In its most basic configuration, computing device 100 typically includes at least one processing unit 102 and memory 104. Depending on the exact configuration and type of computing device, memory 104 may be volatile (such as RAM), non-volatile (such as ROM, flash memory, etc.) or some combination of the two. This most basic configuration is illustrated in FIG. 1 by dashed line 106. Additionally, device 100 may also have additional features/functionality. For example, device 100 may also include additional storage (removable and/or non-removable) including, but not limited to, magnetic or optical disks or tape. Such additional storage is illustrated in FIG. 1 by removable storage 108 and non-removable storage 110. Computer storage media includes volatile and nonvolatile, removable and non-removable media implemented in any method or technology for storage of information such as computer readable instructions, data structures, program modules or other data. Memory 104, removable storage 108 and non-removable storage 110 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can accessed by device 100. Any such computer storage media may be part of device 100.

Device 100 may also contain communications connection(s) 112 that allow the device to communicate with other devices. Communications connection(s) 112 is an example of communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. The term computer readable media as used herein includes both storage media and communication media.

Device 100 may also have input device(s) 114 such as keyboard, mouse, pen, voice input device, touch input device, camera, etc. Output device(s) 116 such as a display, speakers, printer, etc. may also be included. All these devices are well know in the art and need not be discussed at length here.

The present medical image compression and decompression technique may be described in the general context of computer-executable instructions, such as program modules, being executed by a computing device. Generally, program modules include routines, programs, objects, components, data structures, etc. that perform particular tasks or implement particular abstract data types. The present technique may also be practiced in distributed computing environments where tasks are performed by remote processing devices that are linked through a communications network. In a distributed computing environment, program modules may be located in both local and remote computer storage media including memory storage devices.

2.0 COMPRESSION AND DECOMPRESSION OF MEDICAL IMAGES

The exemplary operating environment having now been discussed, the remaining parts of this description section will be devoted to a description of the program modules embodying the present technique for compressing and decompressing medical images. Generally, this technique exploits the fact that medical images within the same category will exhibit a very high level of similarity to each other. For each category, a type of standard image is computed which represents typical characteristics of images within a category. For each image being compressed, only the difference between the image and the standard image is compressed. Due to the high level of similarity between images in the same category, the aforementioned difference is typically small and therefore a high compression ratio can be achieved.

Figure 2:
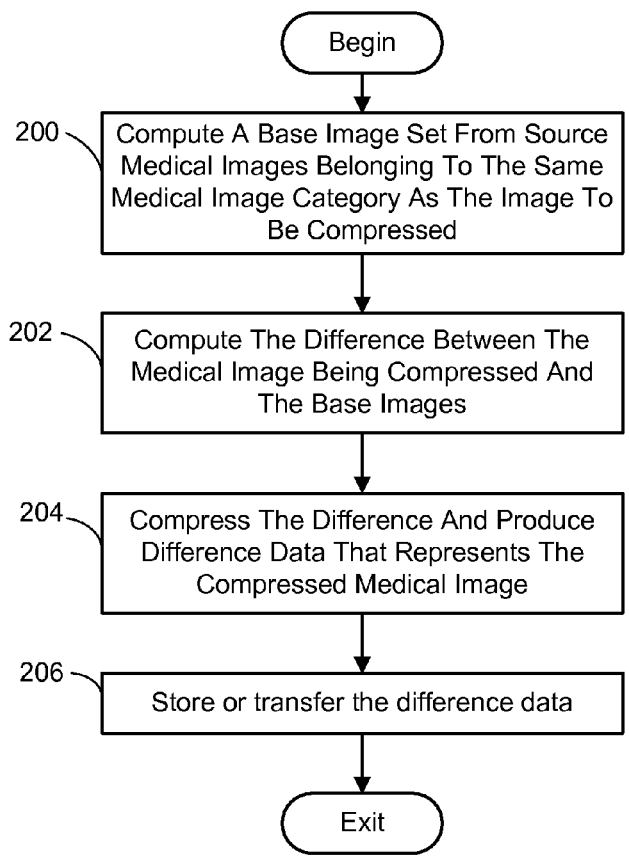
FIG. 2 is a flow diagram generally outlining one embodiment of a process for compressing medical images in accordance with the present medical image compression and decompression technique.

Referring to FIG. 2, the compression portion of the present technique generally involves first computing a set of base images from a group of medical images belonging to the same medical image category—a category which corresponds to the image that it is desired to compress (200). The set of base images collectively act as the aforementioned standard image for the associated medical image category, and will be described in more detail below. The image categories themselves and the source of the group of medical images will also be described in more detail shortly. Once the base image set is computed, the difference between the medical image being compressed and the base images is computed (202). This difference is then compressed and used to produce difference data that represents the compressed medical image (204). The composition of the difference data will be described later in this specification. Finally, the difference data is stored for future use or transferred (208).

Figure 3:
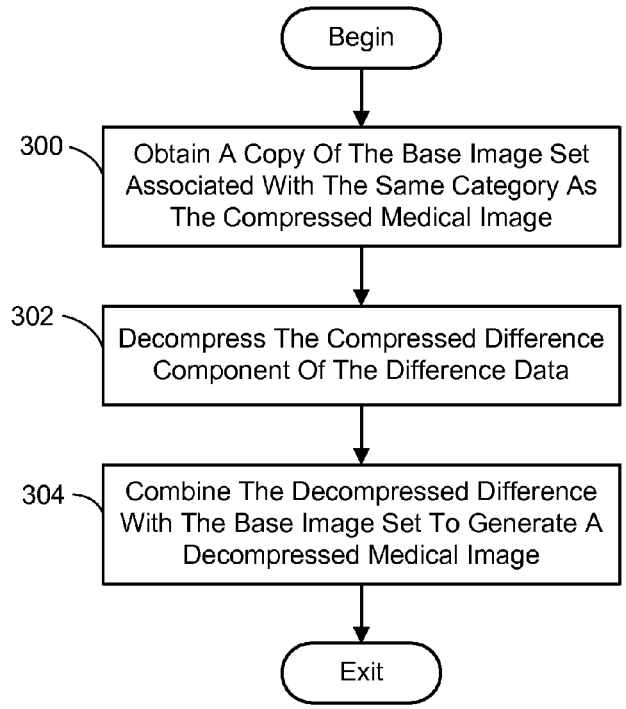
FIG. 3 is a flow diagram generally outlining one embodiment of a process for decompressing a medical image compressed in accordance with the process outlined in FIG. 2.

Referring to FIG. 3, the decompression portion of the present technique generally involves first obtaining a copy of the base image set associated with the same category as the compressed medical image it is desired to decompress (300). The base image set can be obtained in a variety of ways as will be discussed later in this specification. Once the base image set is obtained, the compressed difference component of the difference data representing the compressed medical image is decompressed (302). The decompressed difference is then combined with the base images to generate a decompressed medical image (304).

It is noted that the aforementioned base image sets computed for each medical image category of interest to a user can be generated in advance to save time in the compression and decompression procedure. More particularly, in one embodiment this involves inputting medical images of various categories of interest from a source of medical images. Many such sources in the form of medical image databases currently exist. The source images are then categorized. From the source images in each category, a set of base images is computed for that category. A unique identifier is assigned to each set of base images computed and each base image set is annotated with its identifier. These identifier-annotated sets of base images are then made available for compression and decompression purposes, as will be described in more detail later.

2.1 Medical Image Compression and Decompression Architecture

Figure 4:
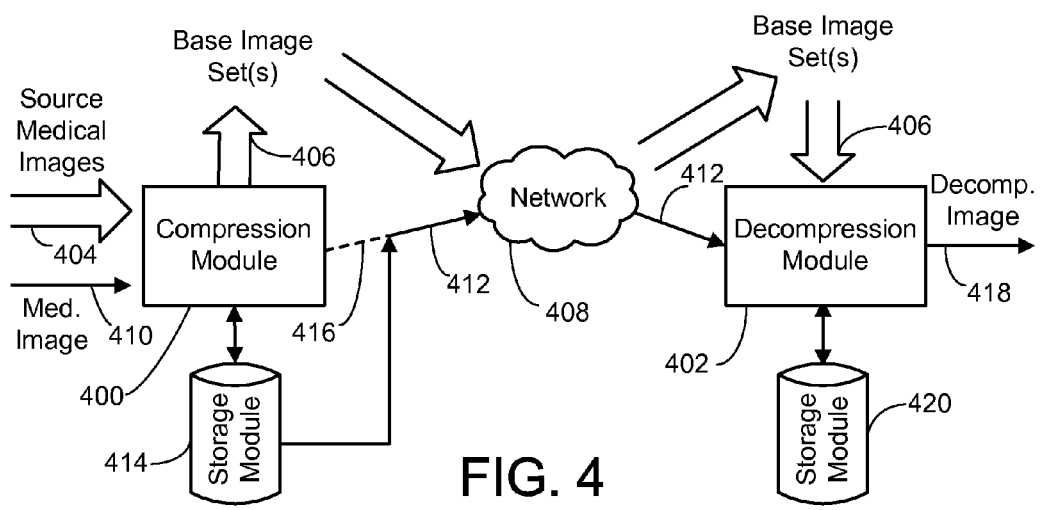
FIG. 4 is a block diagram depicting an idealized architecture for implementing the present technique.

In general, the present medical image compression and decompression technique is embodied in an architecture that in one embodiment includes a compression module (400) and a decompression module (402), as shown in FIG. 4. These modules would run on one or more computing devices, such as those described in the foregoing computing environment section. In a pre-compression phase, the compression module (400) takes in the aforementioned source medical images (404) and generates the base images sets (406) from them. The base image sets (406) are then made available for use in both compression and decompression of medical images. To facilitate their use in decompression, the compression module (400) outputs the base image sets (406) as illustrated in FIG. 4. This can entail a direct transfer to a decompression module (402) via a computer network (408), such as the Internet or an intranet. Alternately, the compression module could output to a computer acting as a server (not shown) on a computer network (408). The decompression module (402) would then include a capability to retrieve copies of the base image sets (406) from the server via the network (408). Another possibility not shown in FIG. 4, is that the base image sets (406) could be stored on any type of computer storage media such as described in the computing environment section, which would then be made accessible to the decompression module (402).

In a compression phase, the compression module (400) takes in a medical image (410) that it is desired to compress. The image (410) is then compressed using the base image set associated with the same category as the medical image. The compressed medical image (412) is then stored in a storage module (414) of any desired configuration that is available to the compression module (400). The compressed image (412) would be transferred from the storage module (414) and sent to a decompression module (402) whenever it is desired to decompress it. Alternately, the compressed image (412) might be transferred directly from the compression module (400) to the decompression module (402), in addition to storing it, as shown in FIG. 4 by the dashed line (416). Here again, the compressed medical image (412) could be sent via a computer network, either directly or via a server. Alternately, the compressed medical image (412) could be stored on any type of computer storage media (not shown) and then be made accessible to the decompression module (402).

In a decompression phase, the decompression module (402) inputs a compressed medical image (412), along with a base image set associated with the same medical image category as the compressed image. It is noted that the base image set could be input on an as needed basis based on the category of the compressed medical image, or one or more base image sets, up to the number generated by the compression module, could be input in advance of inputting the medical image and stored locally. This latter scenario has the advantage of increasing the speed an image can be decompressed, but at the expense of storage space. If it is known what categories of images that are most likely to be decompressed, the decompression module can pre-download just the base image sets associated with those medical image categories.

Once the compressed medical image (412) and at least the base image set associated with the same medical image category as the compressed image, are input, the compressed image is decompressed using the associated base image set. It is noted that the decompression module (402) can store the base image set or sets. If so, storage module (420) would be employed, and can be of any desired configuration that is available to the decompression module (402).

As indicated previously, the foregoing architecture can be employed in implementing the present medical image compression and decompression technique in three phases—namely pre-compression, compression and decompression. Each of these phases will now be described in more detail in the sections to follow.

2.2 Pre-Compression Phase

The purpose of the pre-compression phase is to generate a base image set for each medical image category of interest to the user of the present compression/decompression technique, prior to compressing images. This can be accomplished immediately before a medical image is to be compressed, or a significant amount of time before compression is to take place. It is noted that the base image sets are computed just once and continually re-used to compress medical images thereafter.

Figure 5:
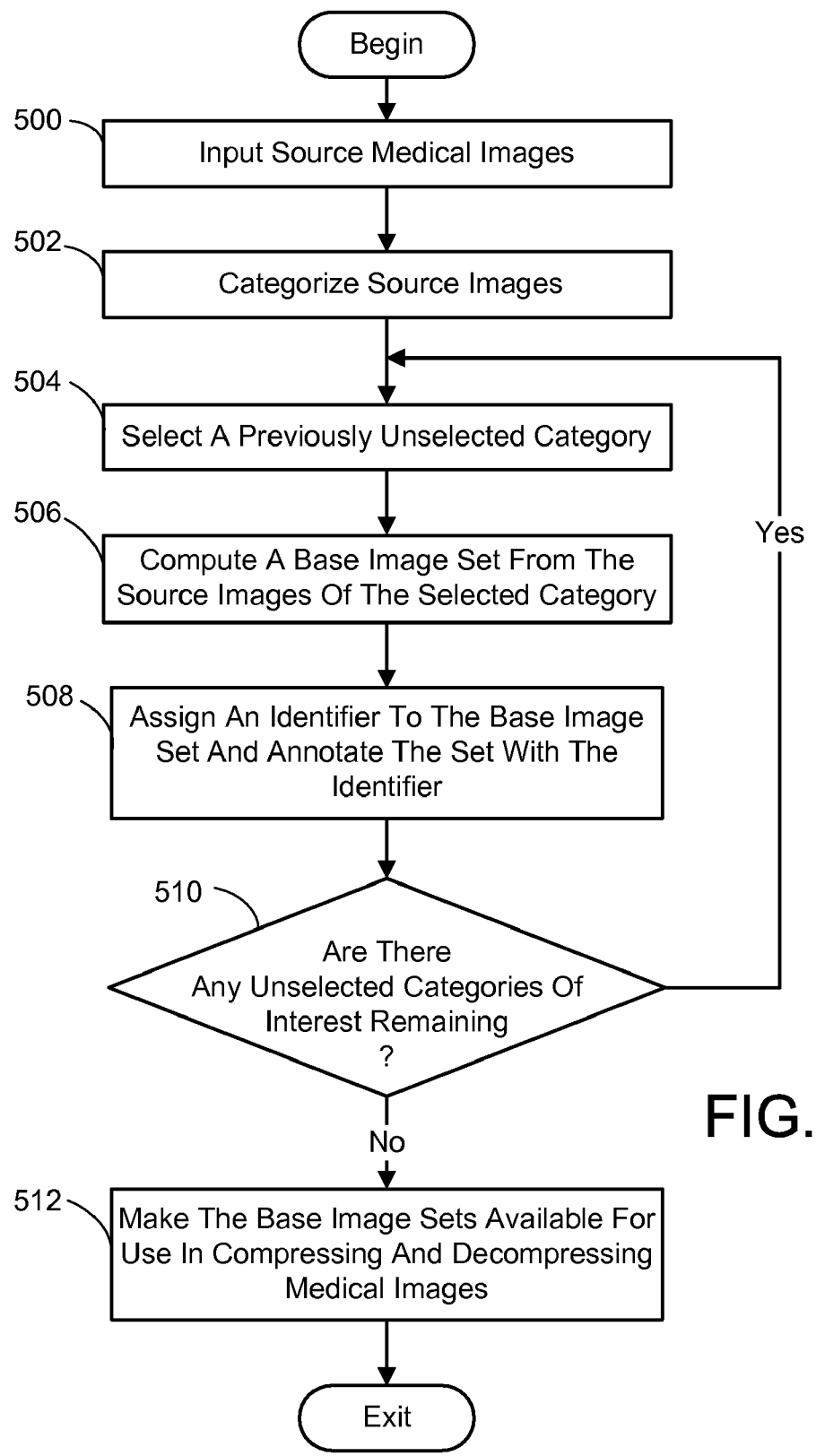
FIG. 5 is a flow diagram outlining one embodiment of a process for a pre-compression phase of the present technique.

Referring to FIG. 5, one embodiment of the pre-compression phase involves first inputting the aforementioned source medical images (500). These source images are chosen so that at least a minimum prescribed number of each of the desired medical image categories is represented. For example, in tested embodiments of the present technique, between 200 and 1000 images were used to generate a base image set for each image category. The medical images are obtained in a conventional manner from any number of medical image databases currently available. For example, commercially available Picture Archiving and Communication Systems (PACS) databases maintained by many medical imaging equipment manufacturers would be a good source for the medical images. These databases contain digital image files each of which has been annotated with characterizing metadata. For instance, by way of example and not limitation, these characterizations can include:

a) the type of image, such as CR/CT, MRI, Ultasound, PET, X-ray, Angiography, and so on;

b) the body part(s) or region that are the subject of the image (e.g., chest, abdomen, foot, and so on);

c) the gender of the patient;

d) the manufacturer and model of the equipment used to capture the image; and e) the resolution and pixel format of the image.

Typically, the characterizing metadata is in accordance with the Digital Imaging and Communications in Medicine (DICOM) standard.

Owing to the large number of images that typically exist in the aforementioned databases, it is desirable to just input those of interest. To this end, only those images having characteristics corresponding to the desired categories would be input. Typically, the medical image databases can be searched using one of more of the identifying characteristics, thereby allowing a user to input just the desired number of images in the categories corresponding to the type of medical images that are to be compressed.

Once the source medical images are input, they are categorized using standard, well-known image categories (502). The user specifies what characteristic or characteristics a source image needs to have to qualify for a particular category. A previously unselected category is then selected (504) and a base image set is computed from the source images associated with the selected category (506). Each base image set computed includes a prescribed number of images that collectively capture the variance exhibited amongst the source images to a substantial degree. In addition, each image within a particular base image set is orthogonal to each other in that for any pair of images in the set, the dot product of vectors formed by concatenating the pixel values in each image is equal to zero. In tested embodiments, these characteristics were obtained using either a Singular Value Decomposition (SVD) procedure or a Principal Component Analysis (PCA) procedure. However, it is not intended to limit the present technique to just these two procedures. Any method that can produce base images having the foregoing characteristics can be employed as well. In tested embodiments, the prescribed number of images that were generated for each base image set varied between 12 and 16 with acceptable results, although numbers above or below this range can be employed as desired. It is noted that the SVD and PCA methods include a precursor procedure where before base images are computed from a group of images, an average image is computed for the group. The value of each pixel in the average image is the average value of all correspondingly located pixels from the group of images. The average image is subtracted from each image in the group of images, on a pixel-by-pixel basis. The SVD or PCA method is then applied to the resulting subtraction images. The average image will be needed to compress and decompress medical images according to the present technique. Therefore, the average image is included in the base image set.

Referring again to FIG. 5, the newly generated base image set is assigned a unique identifier and the set is annotated with this identifier (508). It is then determined if there are any remaining unselected medical image categories of interest (510). If so, actions 504 through 510 are repeated until all the categories of interest have a base image set associated with them. When no more categories remain, the base image sets are made available for use in compressing and decompressing medical images (512), and the pre-compression phase ends. As described previously, base image sets can be made available through a computer network, either directly or via a server. Or alternately, the base image sets could be made available by storing them on any type of computer storage media. Still further, the base image sets could be established as an industrial standard.

2.3 Compression Phase

Figure 6A:
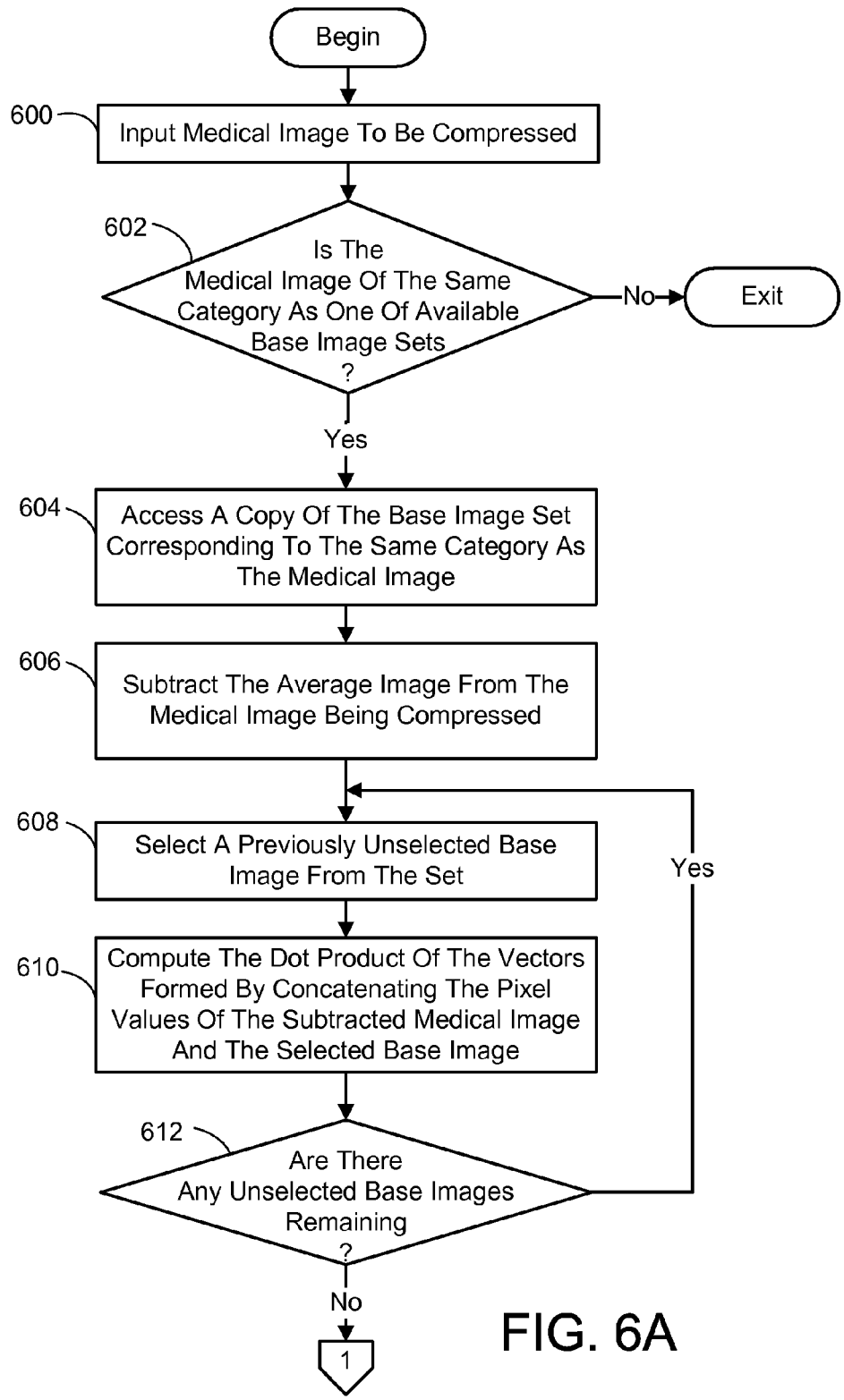
FIGS. 6A-C are a continuing flow diagram outlining one embodiment of a process for the compression phase of the present technique.
Figure 6B:
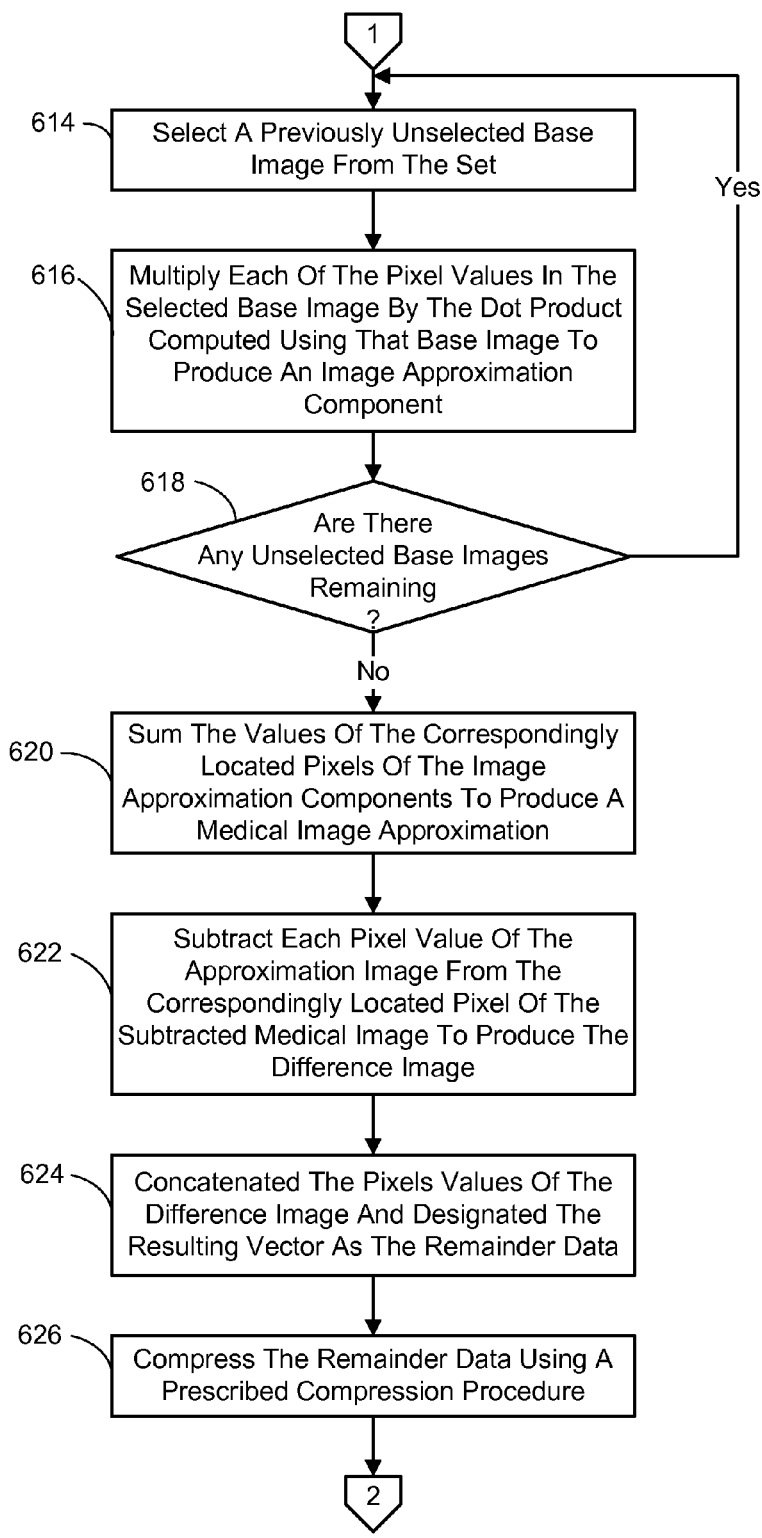
Figure 6C:
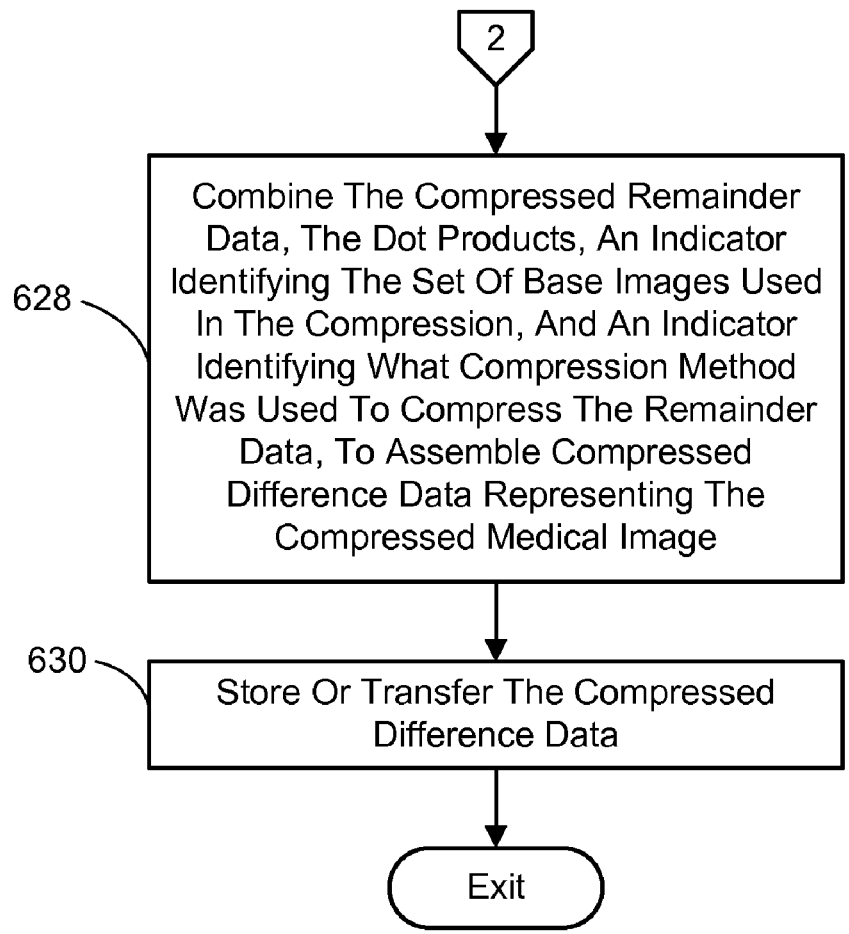

Once the base image sets are computed and made available, a medical image of the same category as one of the sets can be compressed. Referring to FIGS. 6A-C, in one embodiment of the present technique this compression involves first inputting the medical image it is desired to compress (600). The medical image is similar to the source images in that it is a digital image file annotated with the same type of characterizing metadata (e.g., DICOM). Next, it is determined if the medical image is of the same category as one of available base image sets (602). If not, the image cannot be compressed and the procedure ends. On the other hand if the medical image's category does match one of the available base image sets, the matching set is accessed (604). The average image, which is part of the accessed base image set, is subtracted from the medical image being compressed (606). A previously unselected base image in the accessed set is then selected (608), and the dot product of the vectors formed by concatenating the pixel values of the subtracted medical image and the selected base image is computed (610). It is then determined if there are any remaining unselected base images in the set under consideration (612). If so, actions (608) through (612) are repeated. When all the base images have been selected and processed, remainder data is generated using the medical image and the base images. In one embodiment of the present technique, this involves first selecting a previously unselected base image from the accessed set (614) and multiplying each pixel of the selected base image by the previously computed dot product associated with that base image, to generate an image approximation component (616). It is then determined if there are any remaining unselected base images in the accessed set (618). If so, actions (614) through (618) are repeated. When all the base images have been selected and processed, the values of each correspondingly located pixel of the image approximation components are summed to produce an approximation image (620). Each pixel value of the approximation image is then subtracted from the correspondingly located pixel of the subtracted medical image, to produce a difference image (622). The concatenated pixels values of the difference image are designated as the remainder data (624). The remainder data is compressed using a prescribed compression procedure (626). For example, the well-known zlib, bzip, JPEG2000, PNG, GIF, or TIFF compression methods, to name a few, could be employed to compress the remainder data. Next, compressed difference data representing the compressed medical image is assembled by combining the compressed remainder data, the dot products, an indicator identifying the set of base images used in the compression, and an indicator identifying what compression method was used to compress the remainder data (628). The compressed difference data is then stored or transferred as desired (630).

2.4 Decompression Phase

Figure 7A:
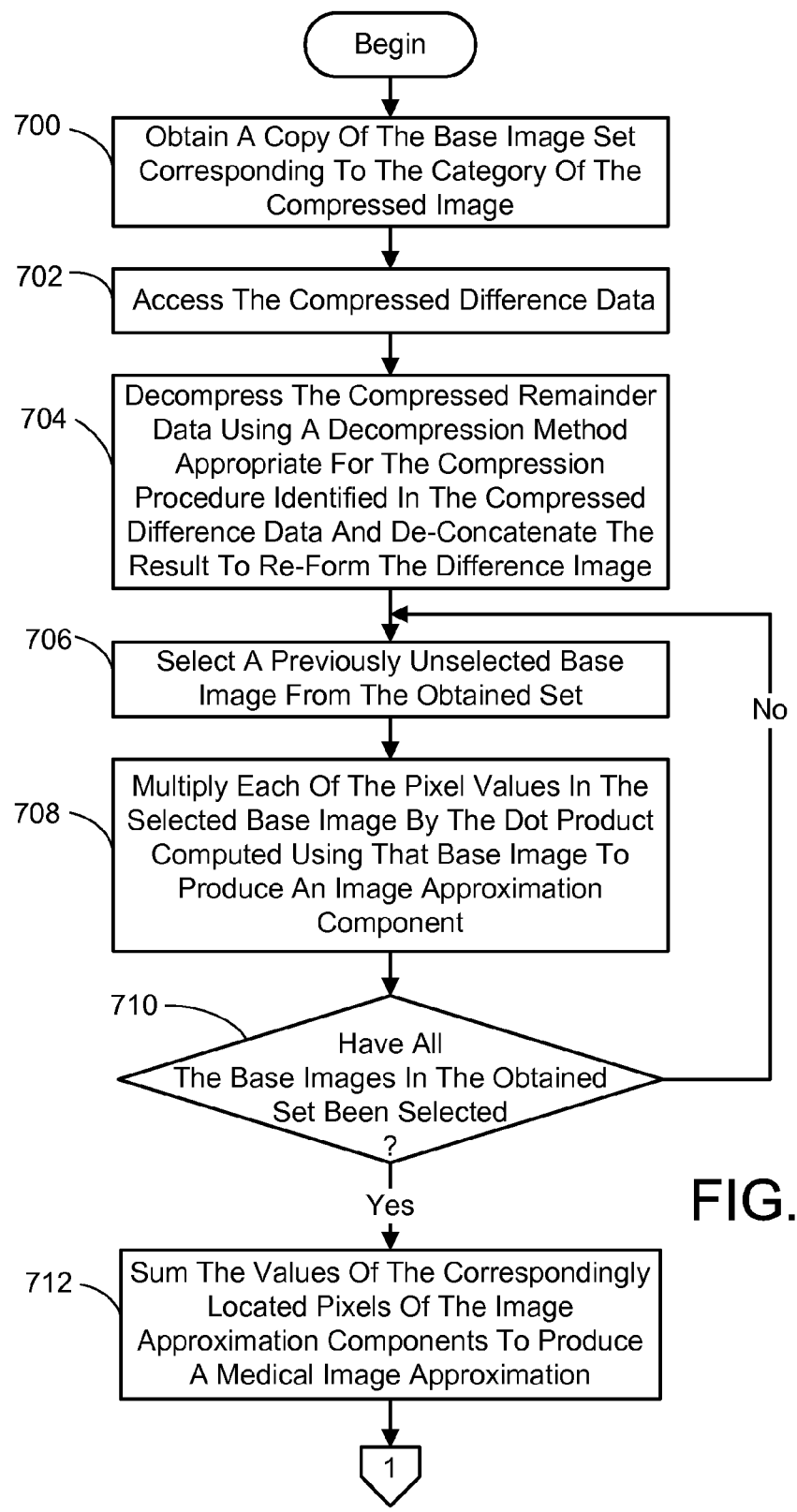
FIGS. 7A-B are a continuing flow diagram outlining one embodiment of a process for the decompression phase of the present technique.
Figure 7B:
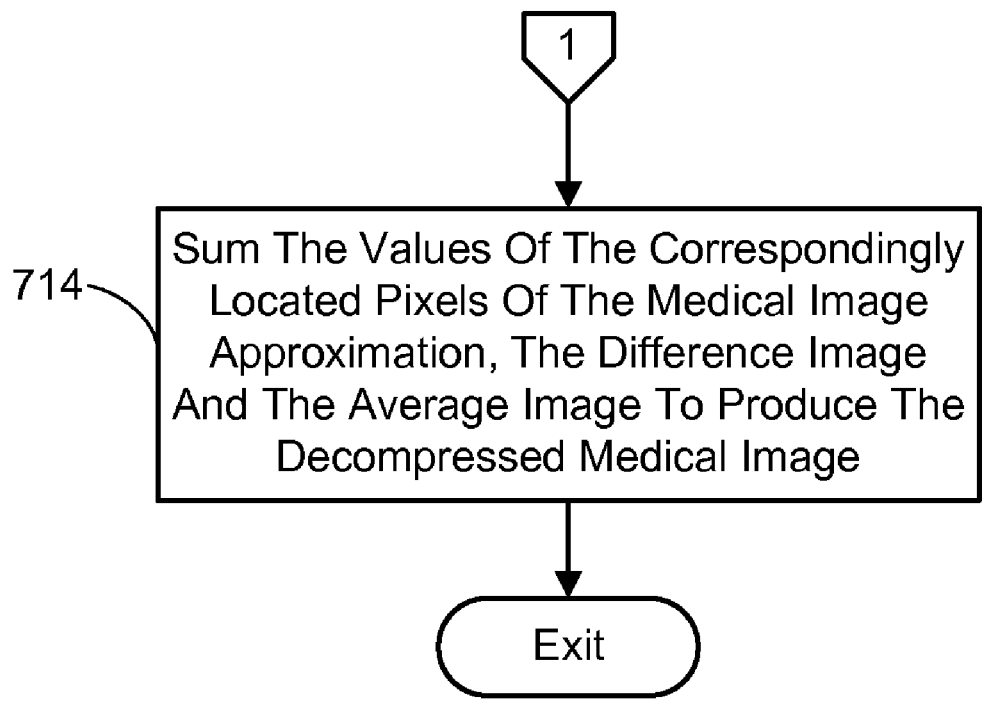

The decompression phase generally involves taking the above-described compressed difference data that represents a compressed medical image and restoring the original medical image using the base image set associated with the same category as the image. More particularly, referring to FIGS. 7A-B, in one embodiment, decompressing a compressed medical image first involves obtaining a copy of the base image set corresponding to the category of the compressed image (700). As indicated previously, obtaining a copy of a base image set can entail downloading the needed set from a computer network or computer storage media at the time of decompression, or downloading base sets of interest in advance and storing them locally. The compressed difference data representing the compressed medical image is then accessed (702). It is noted that if multiple base image sets were pre-downloaded, the set corresponding to the category of the compressed medical image can be identified from the indicator included in the compressed difference data that identifies the correct set. Next, the compressed remainder data is decompressed using a decompression method appropriate for the compression procedure identified in the compressed difference data as having been used to compress the remainder data, and de-concatenated to re-form the aforementioned difference image (704). A previously unselected base image in the obtained set of images is then selected (706), and each of the pixel values in the selected base image is multiplied by the dot product computed using that base image, to produce an image approximation component (708). It is then determined if all the base images in the obtained set have been selected (710). If not, actions (706) through (710) are repeated. When all the base images have been selected and processed, the values of the correspondingly located pixels of the image approximation components are summed to produce an approximation of the medical image being decompressed (712). Next, the values of the correspondingly located pixels of the medical image approximation, the difference image and the average image (which is included in the base image set) are summed to produce the decompressed medical image (714).

3.0 OTHER EMBODIMENTS

It should be noted that any or all of the aforementioned embodiments throughout the description may be used in any combination desired to form additional hybrid embodiments. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Wherefore, what is claimed is:

1. A computer-implemented process for compressing a medical image, comprising using a computer to perform the following process actions:
    computing a set of base images from a larger group of source medical images belonging to a same category as the medical image being compressed, wherein the base image set substantially captures the variance exhibited amongst the group of source images and wherein the base images are orthogonal to each other;
    computing a difference between the medical image being compressed and the base images;
    compressing the difference and producing difference data representing the compressed medical image; and
    storing or transferring the compressed difference data.

2. The process of claim 1, wherein the process action of computing a set of base images, comprises an action of computing the base images using one of (i) a singular value decomposition procedure, or (ii) a principal component analysis procedure.

3. The process of claim 1, wherein the set of base images further comprises an average image which is computed by averaging the values of each correspondingly located pixel in the group of images used to compute the base images, and wherein the process action of computing the difference between the medical image being compressed and the base images, comprises an action of, for each base image in turn, computing the dot product of vectors formed by concatenating the pixel values of a subtracted version of the medical image being compressed and the base image under consideration, wherein the subtracted medical image is computed by subtracting the average image from the medical image on a correspondingly located pixel-by-pixel basis.

4. The process of claim 3, wherein the process action of computing the difference between the medical image being compressed and the base images, further comprises the actions of:
    computing, for each base image in the set, the product of each pixel of the base image under consideration and the previously computed dot product associated with that base image, to generate an image approximation component;
    summing the values of each correspondingly located pixel of the image approximation components to produce an approximation image;
    subtracting the value of each pixel of the approximation image from the correspondingly located pixel of the subtracted medical image, to produce a difference image; and
    concatenating the pixels values of the difference image to produce remainder data.

5. The process of claim 4, wherein the process action of compressing the difference data comprises the actions of:
    compressing the remainder data using a prescribed compression procedure; and
    generating compressed difference data as a combination of the dot products, the compressed remainder data, indicators identifying the set of base images used, and an indicator identifying the prescribed compression procedure.

6. The process of claim 1, wherein the group of source medical images is obtained from a medical image database wherein each image file in the database has been annotated with characterizing metadata which identifies what category the image belongs to, thereby facilitating obtaining only those images having the same category as the medical image being compressed for use in computing the set of base images.

7. The process of claim 6, wherein said medical image database is a Picture Archiving and Communication Systems (PACS) database.

8. The process of claim 6, wherein the group of source medical images obtained from the medical image database are annotated with categorizing metadata according to the Digital Imaging and Communications in Medicine (DICOM) standard.

9. The system of claim 8, wherein the program module for computing the set of base images from source images under consideration, comprises a sub-module for using between 200 and 1000 source medical images to compute the set of base images.

10. The system of claim 8, wherein the program module for computing the set of base images from source images under consideration, comprises computing between 12 and 16 base images.

11. The system of claim 8, wherein the program module for making the identifier-annotated set of base images associated with each category of source images available for decompression purposes, comprises a sub-module for publishing the base image sets to an internet or intranet site.

12. The system of claim 8, wherein the program module for compressing the medical image using the base image set corresponding to the same category as the image being compressed, comprises sub-modules for:
    identifying the category of the medical image being compressed;
    respectively computing a difference between the medical image being compressed and the base images of the set corresponding to the same category as the medical image being compressed, to produce difference data; and
    compressing the difference data.

13. The system of claim 8, further comprising program modules for:
    accessing the base image set corresponding to the same category as the compressed medical image it is desired to decompress;
    accessing the compressed medical image; and
    decompressing the compressed medical image using the accessed base image set.

14. The system of claim 13, wherein the program module for accessing the base image set, comprises sub-modules for:
    obtaining copies of base image sets of interest including the one corresponding to the same medical image category as the compressed medical image it is desired to decompress before accessing the compressed medical image;
    locally storing the copies of the base image sets.

15. The system of claim 13, wherein the compressed medical image comprises a compressed version of a difference between the medical image and the base images of the accessed set, and wherein the program module for decompressing the compressed medical image using the accessed base image set, comprises sub-modules for:
  decompressing the compressed version of the difference between the medical image and the base images of the accessed set to obtain difference data; and
  combining the difference data with the base images of the accessed set to generate a decompressed version of the medical image.

16. A system for compressing and decompressing medical images, comprising:
  a general purpose computing device;
  a computer program comprising program modules executable by the computing device, wherein the computing device is directed by the program modules of the computer program to,
    prior to inputting a medical image for compression,
      input source medical images of various categories,
      categorize the input source images,
      for each category of source images,
        compute a set of base images from the source images under consideration, wherein the base image set substantially captures the variance exhibited amongst the source images under consideration and wherein the base images are orthogonal to each other,
        assign a unique identifier to the set of base images computed using the source images under consideration and annotating the base image set with the identifier,
      make the identifier-annotated set of base images associated with each category of source images available for compression and decompression purposes,
    input and compress a medical image using the base image set corresponding to the same category as the image being compressed, and
    store or transfer the compressed medical image.

17. The system of claim 16, wherein the source medical images are obtained from a medical image database wherein each image file in the database has been annotated with characterizing metadata which identifies characteristics of each image, and wherein the program module for inputting source medical images of various categories, comprises a sub-module for inputting only those source medical images that based on the characterizing metadata belong to categories it is anticipated the images which are to be compressed will share.

18. A computer-implemented process for decompressing a compressed medical image, wherein the compressed medical image was compressed in a manner comprising,
  computing a set of base images from a larger group of source medical images belonging to a same category as the medical image being compressed, wherein the base image set substantially captures the variance exhibited amongst the group of source images and wherein the base images are orthogonal to each other,
  computing a difference between the medical image being compressed and the base images,
  compressing the difference and producing difference data representing the compressed medical image,
and wherein the decompressing process comprises using a computer to perform the following process actions:
  obtaining the set of base images belonging to a same category as the compressed medical image;
  decompressing the compressed difference associated with the compressed medical image; and
  combining the decompressed difference with the set of base images to generate a decompressed medical image.

19. The process of claim 18, wherein the compressed difference comprises,
  for each base image used in the compression, a dot product of the vectors formed by concatenating the pixel values of a subtracted version of the medical image that was compressed and the base image under consideration, wherein the subtracted medical image is computed by subtracting an average image from the medical image on a correspondingly located pixel-by-pixel basis, and wherein the average image is included in the set of base images and was computed by averaging the values of each correspondingly located pixel in the group of images used to compute the base images,
  compressed remainder data generated by,
    computing, for each base image in the set, the product of each pixel of the base image under consideration and the dot product associated with that base image, to generate an image approximation component,
    summing the values of each correspondingly located pixel of the image approximation components to produce an approximation image,
    subtracting the value of each pixel of the approximation image from the correspondingly located pixel of the subtracted medical image, to produce a difference image,
    concatenating the pixels values of the difference image to produce remainder data, and
    compressing the remainder data using a prescribed compression procedure,
  a compression procedure indicator identifying the procedure used to compress said remainder data, and
  an base image set indicator identifying the base images used in the compression,
and wherein the process action of decompressing the compressed difference associated with the compressed medical image, comprises the actions of:
  decompressing the compressed remainder data using a decompression procedure appropriate for the compression procedure identified by the compression procedure indicator; and
  de-concatenating the decompressed remainder data to reform the difference image.

20. The process of claim 19, wherein the process action of combining the decompressed difference data with the set of base images, comprises the actions of:
  for each base image, multiplying each of the pixel values in the base image under consideration by the dot product computed using that base image and to generate a medical image approximation component;
  summing the pixel values of the correspondingly located pixels of the medical image approximation components to generate an approximation of the medical image being decompressed; and
  summing the pixel values of the correspondingly located pixels of the medical image approximation, the difference image and the average image.

* * * * *